United States Patent
Tuan

(10) Patent No.: US 11,045,538 B2
(45) Date of Patent: Jun. 29, 2021

(54) METHOD AND COMPOSITION FOR TREATMENT OF HYPERGLYCEMIA

(71) Applicant: Mei-Nan Tuan, Taipei (TW)

(72) Inventor: Mei-Nan Tuan, Taipei (TW)

( * ) Notice: Subject to any disclaimer, the term of this patent is extended or adjusted under 35 U.S.C. 154(b) by 0 days.

(21) Appl. No.: 16/661,789

(22) Filed: Oct. 23, 2019

(65) Prior Publication Data

US 2020/0121778 A1    Apr. 23, 2020

Related U.S. Application Data

(60) Provisional application No. 62/749,287, filed on Oct. 23, 2018.

(51) Int. Cl.
| | | |
|---|---|---|
| *A61K 39/085* | (2006.01) | |
| *A61P 3/10* | (2006.01) | |
| *A61K 36/48* | (2006.01) | |
| *A61K 36/9066* | (2006.01) | |

(52) U.S. Cl.
CPC ............ *A61K 39/085* (2013.01); *A61K 36/48* (2013.01); *A61K 36/9066* (2013.01); *A61P 3/10* (2018.01)

(58) Field of Classification Search
None
See application file for complete search history.

(56) References Cited

U.S. PATENT DOCUMENTS

2003/0180399 A1* 9/2003 Chauhan ............ A61K 2300/00
424/735

OTHER PUBLICATIONS

Guo et al. Central European Journal of Immunology, 40(3), and 2015. (Year: 2015).*
Kawamura et al. Journal of Immunology, vol. 15, No. 8, pp. 4362-4370, 1993. (Year: 1993).*

* cited by examiner

*Primary Examiner* — Jana A Hines
*Assistant Examiner* — Khatol S Shahnan Shah
(74) *Attorney, Agent, or Firm* — Birch, Stewart, Kolasch & Birch, LLP

(57) ABSTRACT

The present invention provides a method for treatment of hyperglycemia, particularly type 2 diabetes with Staphylococcal enterotoxins (SE). Also provided are a composition for treatment of hyperglycemia, comprising Staphylococcal enterotoxins, and a use of Staphylococcal enterotoxins for treatment of hyperglycemia.

2 Claims, 2 Drawing Sheets

METHOD AND COMPOSITION FOR TREATMENT OF HYPERGLYCEMIA

CROSS REFERENCE TO RELATED APPLICATIONS

Figure 1:
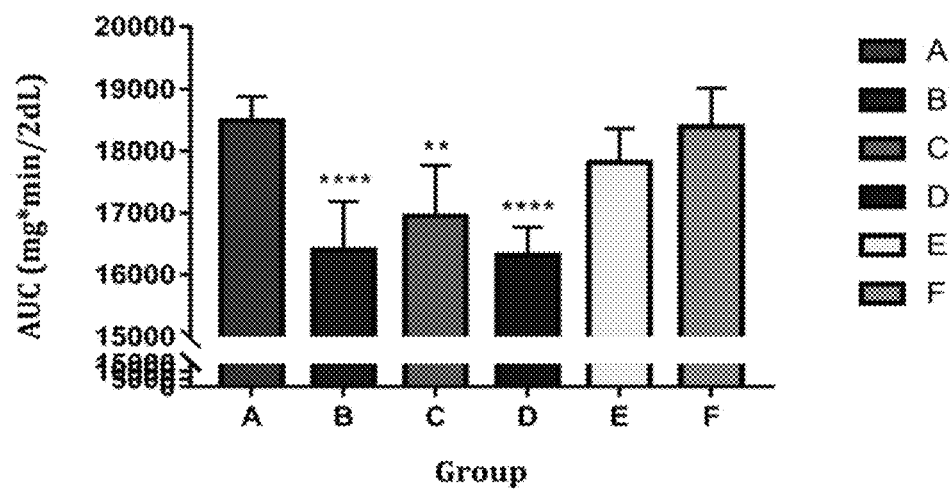

This non-provisional application claims the benefit under 35 U.S.C. § 119(e) to U.S. Provisional Application No. 62/749,287, filed on Oct. 23, 2018, which is hereby expressly incorporated by reference into the present application.

FIELD OF THE INVENTION

The present invention relates to a method and composition for treating hyperglycemia.

BACKGROUND OF THE INVENTION

Diabetes mellitus (DM), also referred to as diabetes, is a metabolic disorder in which there are symptoms of chronic hyperglycemia. Serious long-term complications include cardiovascular disease, stroke, chronic kidney disease, food ulcers and damages to the eyes. There are three types of diabetes mellitus:
(1) Type 1 diabetes, referred to as insulin-dependent diabetes mellitus (IDDM), which results from the pancreas' failure to produce enough insulin due to loss of beta cells;
(2) Type 2 diabetes, referred to as non insulin-dependent diabetes mellitus (NIDDM) or adult-onset diabetes, which begins with insulin resistance, a condition in which cells fail to respond to insulin property;
(3) gestational diabetes, which is the third main form, and occurs when pregnant women without a previous history of diabetes develop high blood sugar levels.

Prevention and treatment strategies include maintaining a healthy diet, regular physical exercise, a normal body weight, and a voiding uses of tobacco. Normally, Type 1 diabetes may be managed with insulin injections, and type 2 diabetes may be treated with medications with or without insulin. However, the treatment for diabetes with insulin would be failed if insulin resistance (IR) occurs in the diabetes patients. Insulin resistance (IR) is a pathological condition in which cells fail to respond normally to insulin. To prevent the development of pathological glucose metabolism and noticeable organ damage over time, the pancreas produces and releases insulin in response to the raise of blood glucose upon digestion of dietary carbohydrates (primarily). This physiological insulin secretion triggers liver to decrease the release of glucose into and facilitates tissue cells to take up glucose from blood stream, therefore allow peripheral tissue cells to utilize blood glucose as energy source and building blocks. The combining physiological responses of insulin on liver and peripheral tissues provide a stringent mechanism to stabilize and regulate postprandial blood glucose concentration Both life style (lack of physical activity) and dietary nutrition (excessive high energy foods) have been implicated in the development of pathological hyperglycemia as a consequence of increased insulin resistance in tissues and reduction in insulin secretion from pancreas beta cells. Current medical interventions of hyperglycemia are focused on reducing carbohydrate absorption, restoring proper insulin secretion from pancreas cells and recovering physiological insulin responses of tissue cells.

Staphylococcal enterotoxins (SE) are representative of a family of proteins, also named as superantigens (SAg), which cause non-specific activation of T lymphocytes (T-cells) resulting in polyclonal T cell activation and massive cytokine release. As compared to a normal antigen-induced T-cell response where 0.0001-0.001% of the body's T-cells are activated, SEs are capable of activating up to 20% of the body's T-cells. SEs are known as the most powerful T-cell mitogens. It has never been disclosed that SE has an effect in decrease of blood glucose in a subject.

It is desirable to develop a new approach for lowering blood glucose in a subject, as in place of the treatment of insulin, particularly a method and composition for treatment of hyperglycemia in a subject with insulin resistance.

BRIEF SUMMARY OF THE INVENTION

It is unexpectedly found in the present invention that Staphylococcal enterotoxins (SE), which is also known as superantigens (SAg), with or without a mixture of plant extracts, leads to a decrease in blood glucose in a subject suffering from type 2 diabetes. This was confirmed by a clinical observation, illustrating that SE could be potentially used to ameliorate hyperglycemia, particularly insulin independent diabetes, such as type 2 diabetes.

In one subject, the present invention provides a method for treatment of hyperglycemia in a subject, comprising administering to said subject Staphylococcal enterotoxins (SE) at a therapeutically effective amount to lower blood glucose in the subject.

In one embodiment of the invention, the subject is one having insulin resistance.

In another aspect, the invention provides a method for treating insulin independent diabetes in a subject, e.g., type 2 diabetes, comprising administering to said subject Staphylococcal enterotoxins (SE) at a therapeutically effective amount to lower blood glucose in the subject.

In one further aspect, the invention provides a use of SE for manufacturing a medicament for treating hyperglycemia.

In one yet aspect, the present invention provides a dietary or pharmaceutical composition for treating hyperglycemia or lowering blood glucose in a subject, which comprises a therapeutically effective amount of SE and a physiologically or pharmaceutically acceptable carrier. In particular, hyperglycemia is an insulin independent diabetes, e.g., type 2 diabetes.

In one example of the invention, the dietary or pharmaceutical composition for treating insulin independent diabetes, e.g., type 2 diabetes, is provided. The composition comprises a therapeutically effective amount of SE and a physiologically or pharmaceutically acceptable carrier.

In one further yet aspect, the present invention provides a combination or composition for treating hyperglycemia, particularly insulin independent diabetes, e.g., type 2 diabetes, which comprises a therapeutically effective amount of SE in combination of an anti-diabetes drug, a substance or a plant extract providing hypoglycemic efficacies, or a mixture thereof.

In one example of the invention, the combination or composition for use in the treatment of hyperglycemia comprises a therapeutically effective amount of SE together with a mixture of plant extracts providing hypoglycemic efficacies, wherein the mixture of plant extracts comprises *Momordica charantia, Curcuma longa*, and/or *Trigonella foenumgraecum.*

BRIEF DESCRIPTION OF THE SEVERAL VIEWS OF THE DRAWINGS

FIG. 1 illustrates the hypoglycemic effect of the mixture of plant extracts and SE on normal mice, wherein mice were oral gavage administrated with various compositions for 3 weeks: Group A treated with the mixture of plant extracts at 0.11 g/0.3 mL, Group B treated with a composition containing the mixture of plant extracts at 0.11 g/0.3 mL and SE at 25 ng/0.3 mL, Group C treated with a composition containing the mixture of plant extracts at 0.11 µg/0.3 mL and SE at 1.4 µg/0.3 mL, Group D treated with SE at 25 ng/0.3 mL, Group E treated with SE at 1.4 ug/0.3 mL, and Group F treated with the vehicle without any therapeutic agent (Control). Mice were fasted for 10 hours and then performed OGTT for 120 min. every week. Data were shown as mean±standard error (SE). Significant analysis was used a one-way ANOVA with Tukey's test to determine the difference in treatments as compared with the untreated control. A data histogram was built using GraphPad Prism 7.04 (La Jolla, Calif., USA).  ($p<0.01$) and ** ($p<0.0001$) significant level.

Figure 2:
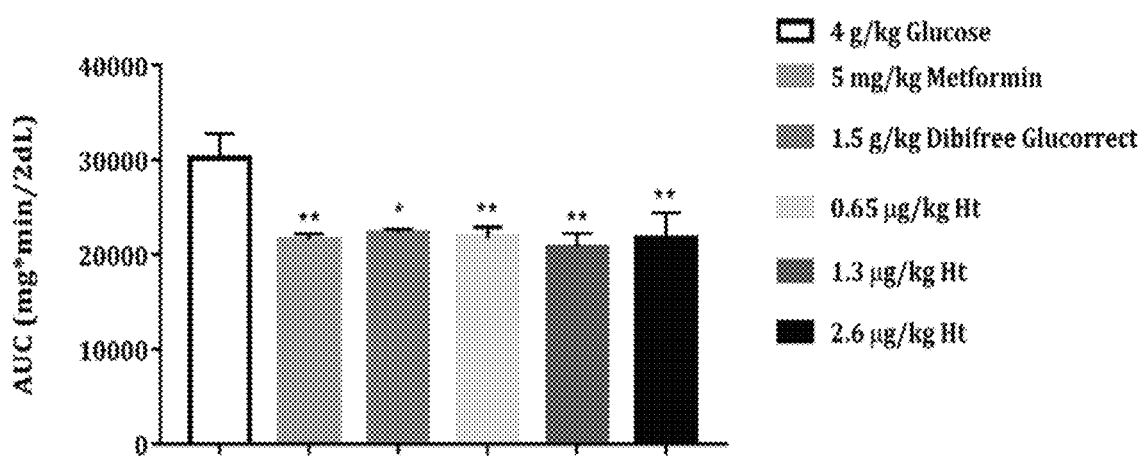

FIG. 2 shows the hypoglycemic effect of the compositions at various concentrations of SE on normal mice; wherein mice were oral gavage administrated with the compositions containing SE at 8 ng/0.3 mL(A), 24 ng/0.3 mL (B), 40 ng/0.3 mL (C), 120 ng/0.3 mL(D), E (240 ng/0.3 mL (E) and vehicle, control F (F) for 1 week. Mice were fasted for 10 hours and performed OGTT for 120 min. at the end of one week. Data were shown as mean±standard error (SE). Significant analysis are used a one-way ANOVA with Tukey's test to determine the difference in treatments as compared with the untreated control. A data histogram was built using GraphPad Prism 7.04 (La Jolla, Calif., USA). * ($p<0.05$) significant level.

Figure 3:
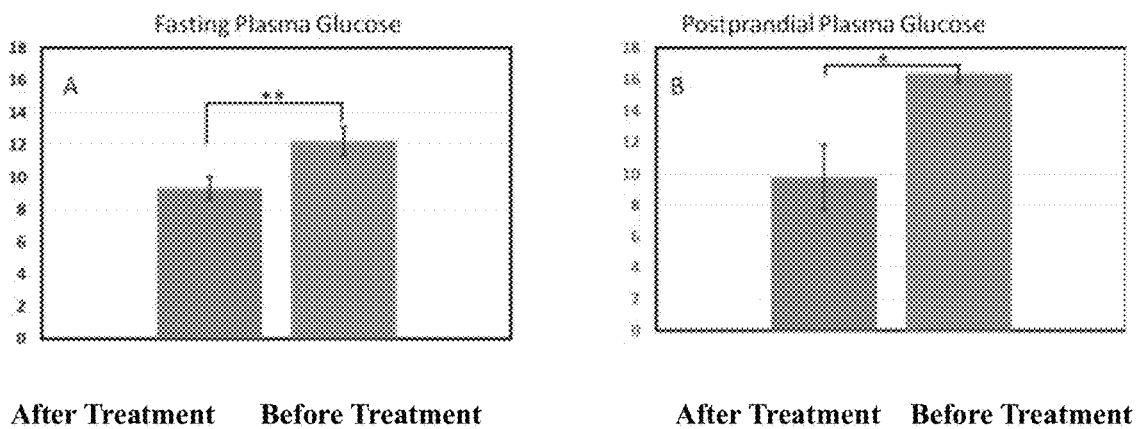

FIG. 3 provides the result of Case 1 in the clinical observation, showing the efficacy of the administration of the composition containing SE in place of anti-diabetic medicines. After the treatment of a composition containing SE in the diabetes patient, the levels of the blood glucose (After Treatment) were significantly lower than those of the patient before the treatment of the composition containing SE according to the invention (Before Treatment).

Figure 4:
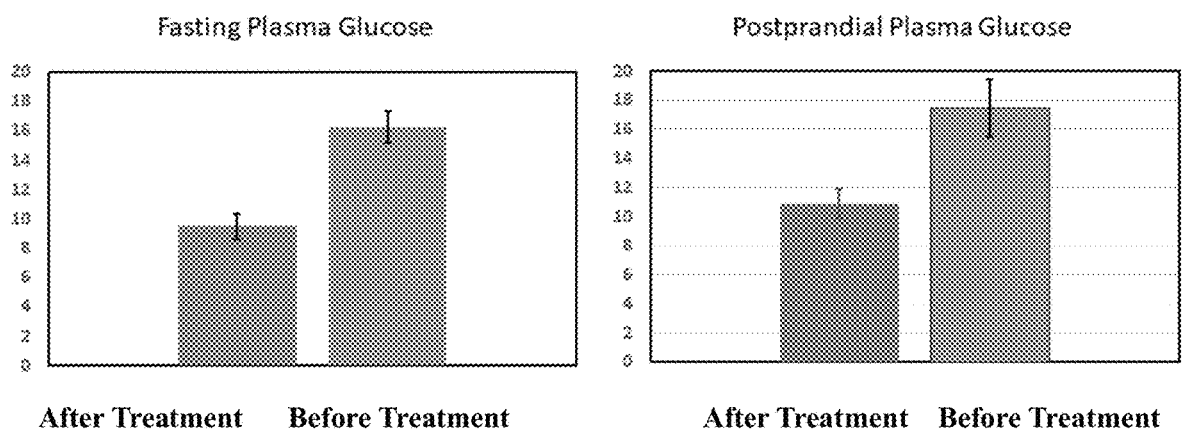

FIG. 4 provides the result of Case 2 in the clinical observation, showing the efficacy of the administration of the composition containing SE in place of anti-diabetic medicines. After the treatment of a composition containing SE in the diabetes patient, the levels of the blood glucose (After Treatment) were significantly lower than those of the patient before the treatment of the composition containing SE according to the invention (Before Treatment).

Figure 5:
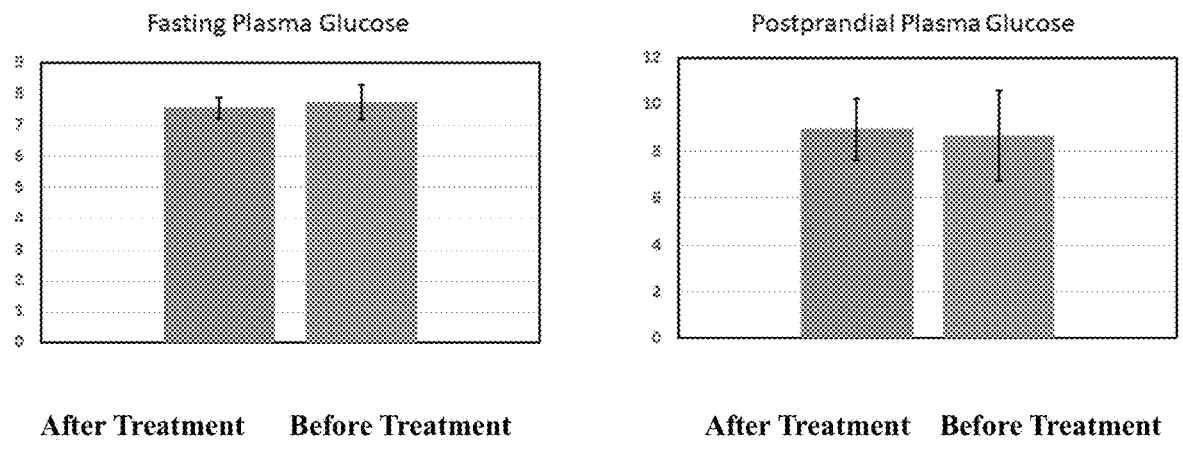

FIG. 5 provides the result of Case 3 n the clinical observation, showing the efficacy of the administration of the composition containing SE in place of anti-diabetic medicines. After the treatment of a composition containing SE in the diabetes patient, the levels of the blood glucose (After Treatment) maintained those of the patient before the treatment of the composition containing SE according to the invention (Before Treatment).

DETAILED DESCRIPTION OF THE INVENTION

Unless otherwise defined herein, scientific and technical terms used herein have the meanings that are commonly understood by those of ordinary skill in the art.

The present invention provides a new approach for treatment hyperglycemia, particularly in a subject having insulin resistance, or for treatment of type 2 diabetes. It was confirmed that the levels of blood glucose in the diabetes patients were maintained as a normal level or even decreased after the oral administration of the composition containing SE according to the invention, with and without a mixture of plant extracts. Accordingly, SE may be used to ameliorate hyperglycemia, in particular insulin independent diabetes (e.g., type 2 diabetes).

The present invention provides a method and a composition for treatment of hyperglycemia, particularly insulin independent diabetes, e.g., type 2 diabetes. The method comprises administering to a subject in need thereof Staphylococcal enterotoxins (SE) at a therapeutically effective amount to lower blood glucose in the subject.

Furthermore, the present invention provides a use of SE for manufacturing a medicament for treating hyperglycemia, particularly insulin independent diabetes, e.g., type 2 diabetes.

According to the invention, the composition of SE may be administered in combination of an anti-diabetes drug, a substance or plant extract providing hypoglycemic efficacies, or a mixture thereof.

The term "subject" as used therein refers to a person, multiple persons, an animal or multiple animals.

The term "Staphylococcal enterotoxins" or "SE" as used herein refers to one or more proteins of Staphylococcal enterotoxins, a functional variant or fragment thereof; including but not limited to Staphylococcal enterotoxin A (SEA), Staphylococcal enterotoxin B (SEB), Staphylococcal enterotoxin C (SEC), Staphylococcal enterotoxin D (SED) and Staphylococcal enterotoxin E (SEE).

The term "functional variant or fragment" as used herein refers to a variant or fragment having the ability to lower blood glucose, as the same as or similar to Staphylococcal enterotoxins.

The term "therapeutically effective amount" as used herein refers to the amount of the SE of the present invention contained in the composition administered is of sufficient quantity to achieve the intended purpose, such as, in this case, to lower blood sugar in a subject.

Pharmaceutical compositions can be prepared by mixing with optional physiologically or pharmaceutically acceptable carriers, including solvents, dispersion media, isotonic agents and the like. The carrier can be liquid, semi-solid or solid carriers. In some embodiments, carriers may be water, saline solutions or other buffers (such as serum albumin and gelatin), carbohydrates (such as monosaccharides, disaccharides, and other carbohydrates including glucose, sucrose, trehalose, mannose, mannitol, sorbitol, or dextrins), gel, lipids, liposomes, stabilizers, preservatives, antioxidants (including ascorbic acid and methionine), chelating agents (such as EDTA), salt forming counter-ions (such as sodium) or combinations thereof.

In the invention, any of the anti-diabetes drugs, substances or plant extracts, or mixture thereof providing hypoglycemic efficacies may be used in combination of the composition containing SE according to the invention. The anti-diabetes drug may be, including but not limited to metformin, thiazolidinediones and etc. In one example of the present invention, the mixture of the plant extracts contains the extracts of *Momordica charantia, Curcuma longa*, and/or *Trigonella foenumgraecum* or mixture thereof.

In the invention, any plant extracts providing hypoglycemic efficacies can be used. One example is a mixture of various plant extracts, for example, the extracts of *Momordica charantia, Curcuma longa*, and/or *Trigonella foenumgraecum*, which provides hypoglycemic efficacies.

The plant extracts may be prepared by any standard or commonly used methods. For example, the plant extracts may be extracted with water or ethanol.

In addition, it is unexpectedly found in the present invention that a composition of SE in combination of a mixture of plant extracts provides an improved efficacy in lowering blood glucose, wherein the mixture of plant extracts comprises, essentially consists of or consists of, the extracts of *Momordica charantia*, *Curcuma longa* and *Trigonella foenumgraecum*.

The invention is further illustrated by the following example, which should not be construed as further limiting.

Example 1 Animal Experiments 6-week-old male ICR mice were obtained from National Laboratory Animal Center (Taipei, Taiwan) and were kept in controlled environmental conditions at room temperature (22±2° C.) and humidity (55±10%). The 12 h light/dark (0600-1800) cycle was maintained throughout the experiments. The animals had free access to the standard chow (PMI LabDiet 5001; 13.2% fat, 24.7% protein, and 62.1% carbohydrates as a source of calories) and sterilized water ad libitum. Animal experimental protocols were followed as per the "Guide for the Care and Use of Laboratory Animals" of National Dong-Hwa University approved by the National Dong-Hwa University Animal Ethics Committee. In the test period, animals were oral gavage administered with all the test articles each day at 5 PM and OGTT were performed by the end of each week for three weeks. Six mice per group were used for the in vivo studies. The in vivo studies were performed at least twice. The experiment animals (mice) were divided into six groups:

Group A: treated with the plant extracts, 0.33 g/mL;
Group B: treated with the plant extracts, 0.33 g/mL and the SE, 75 ng/mL of SEC in PBS containing 20 mg/mL BSA;
Group C: treated with the plant extracts, 0.33 g/mL and the SE, 4.3 ug/mL of SEC in PBS containing 20 mg/mL BSA;
Group D: treated with the SE, 75 ng/mL of SEC in PBS containing 20 mg/mL BSA;
Group E: treated with the SE, 4.3 ug/mL of SEC in PBS containing 20 mg/mL BSA; and
Group F: control, treated with vehicle.

The following tests were conducted.

1. Oral Glucose Tolerance Test (OGTT)

He experiments were performed at approximately 10 am of test day. For aged 8-12 weeks mice fasted, standard chow was removed at 11 PM on the day of the OGTT for 10 h fasting. All the administered materials were dissolved in isotonic sodium chloride solution (0.9% sodium chloride) containing 20 mg/mL BSA. All the test articles groups were oral gavage administered D-(+)-glucose (3 g/kg of body weight). Blood samples were drawn from the tail vein right before glucose loading (time 0) and at 30, 60, 90, and 120 min after glucose administration. Plasma glucose of test mice was monitored using a glucometer (Accu-Chek blood sugar analyzer, Roche). Glucose $AUC_{0-120}$ was calculated during the 120-min time interval from OGTT results. Glucose $AUC_{0-120}$ was obtained using the formula $AUC_{0-120} = [30 \times (G_0 + G_{30})/2] + [30 \times (G_{15} + G_{30})/2] + [30 \times (G_{30} + G_{60})/2] + [30 \times (G_{60} + G_{90})/2] + [30 \times (G_{90} + G_{120})/2]$ where $G_0$, $G_{30}$, $G_{60}$, $G_{90}$, and $G_{120}$ were blood glucose level at each time point during OGTT.

The data obtained in each of the experiments were presented as mean±standard error. Statistics were performed using one-way analysis of variance (ANOVA) with Tukey's test. A p-value of less than 0.05 was considered to be significant; Significance level is shown in the figures: * $P<0.05$ and ** $P<0.01$.

Results

To test whether Hopkintide (HT) would affect the plasma glucose, we examined the glycemic response of Hopkintide alone or combined with botanic extracts in oral glucose tolerance test (OGTT) of fasted diabetic and normal mice. The effect of test article or vehicle on glucose control was measured by the glucose $AUC_{0-120}$ min which was obtained by integration of glucose level from 0 to 120 min during mice OGTT studies. The hypoglycemic efficacy of test article in mouse OGTT reflected by its reduced $AUC_{0-120\ min}$ as compared to that of vehicle. As shown in FIG. the glucose $AUC_{0-120}$ min of vehicle was measured to be 18394 mg*min/dL while those of test article D and E were 16311 and 17818 mg*min/dL, respectively. When compared with the vehicle, D group showed the significantly ($p<0.05$) lower blood glucose level. The AUCs are significantly reduced in mice administered 0.9 ug/kg but not 51.6 ug/kg of SE. This analysis shows that glucose lowering effect found in mice received a dose at 0.9 ug/kg of SE. This finding reveals that Hopkintide at lower but not in high dose displays a glucose lowering effect in mice OGTT study. As shown in FIG. mice administered with 4 g/kg of plant extract did not show a reduced AUC as compared to that of vehicle group (18490 vs 18394 mg*min/dL). This observation shows that botanic extract alone at a dose of 0.33 g/mL (4 g/kg) did not affect plasma glucose response during mouse OGTT study. The AUC of mice administered with 0.33 g/mL (4 g/kg) of plant extract combined with 0.9 ug/kg and 51.6 ug/kg of SEC were measured to be 16400 and 16950 mg*min/dL, respectively (see FIG. 1). Comparison of these values to that of vehicle group, the result indicates that both dosages of Hopkintide together with 0.33 g/mL (4 g/kg) of botanic extract significantly ($p<0.05$) lower blood glucose during mouse OGTT.

Example 2 Clinical Observation

A clinical observation for three diabetic patients was conducted and the levels of glycated hemoglobin (also knowns as HbA1c) for each patient were recorded. HbA1c is a form of hemoglobin (Hb) that is chemically linked to a sugar, and indicates the presence of excessive sugar in the bloodstream, often indicative of diabetes as it is easy to detect.

Case 1

A 69-year-old male who was diagnosed with diabetes for six years, was treated with an oral anti-diabetic medicine without insulin for four years. Then, he was treated with the composition containing SE according to the invention (the SE treatment) as a replacement for an oral anti-diabetic medicine. The levels of plasma glucose were measured before breakfast (fasting plasma glucose level) and 2 hours after dinner (postprandial plasma glucose) and recorded. The averages of plasma glucose of the last 9 day from the patient without treatment of the anti-diabetic medicines (the negative control) and those of the last 9 day from the patient after a two-month treatment of the composition of SE according to the invention (the SE treatment) in place of the oral medicines. As shown in FIG. 2, the blood glucose was significantly reduced after the SE treatment.

Case 2

A 68-year-old female who was diagnosed with diabetes for six years, was treated with an oral anti-diabetic medicine without insulin for four years. Then, she was treated with the composition containing SE according to the invention (the SE treatment) as a replacement for the oral anti-diabetic medicine. The levels of blood glucose were measured before breakfast (fasting blood glucose level) and 2 hours after dinner (postprandial blood glucose). FIG. 2 illustrates the comparisons between the averages of blood glucose of the last 9 day from the patient before discontinuing the anti-diabetic medicines (the negative control) and that of the last 9 day from patient over two month of treatment of the composition of SE according to the invention (the SE treatment) in place of the oral medicines.

Case 3

A man being 67-year-old who was a diabetes patient for ten years, was treated with oral anti-diabetic medicines without insulin for ten years. Then, he was treated with the composition containing SE according to the invention as a replacement for the oral anti-diabetic medicines. The levels of blood glucose were measured before breakfast (fasting blood glucose level) and 2 hours after dinner (postprandial blood glucose). FIG. 3 illustrates the comparisons between the averages of plasma glucose of the last 9 day from the patient before discontinuing the anti-diabetic medicines (the negative control) and that of the last 9 day from patient over two month of treatment of the composition of SE according to the invention (the SE treatment) in place of oral medicine.

While the present invention has been disclosed by way preferred embodiments, it is not intended to limit the present invention. Any person of ordinary skill in the art may, without departing from the spirit and scope of the present invention, shall be allowed to perform modification and embellishment. Therefore, the scope of protection of the present invention shall be governed by which defined by the claims attached subsequently.

What is claimed is:

1. A method for treatment of type 2 diabetes, comprising: administering to a subject in need thereof Staphylococcal enterotoxin C (SEC) at a therapeutically effective amount.

2. The method of claim 1, wherein the subject is one having insulin resistance.

\* \* \* \* \*